United States Patent [19]
Therrien

[11] Patent Number: 5,972,343
[45] Date of Patent: Oct. 26, 1999

[54] HAIR AND SCALP NOURISHING COMPOSITION

[76] Inventor: Yoshiko Therrien, 2265 Lee Rd., Suite 223, Winter Park, Fla. 32789

[21] Appl. No.: 09/119,105

[22] Filed: Jul. 20, 1998

[51] Int. Cl.⁶ ...................................................... A61K 35/78
[52] U.S. Cl. ........................................ 424/195.1; 424/94.2
[58] Field of Search ................................ 424/195.1, 94.2

[56] References Cited

U.S. PATENT DOCUMENTS

| | | | |
|---|---|---|---|
| 5,128,139 | 7/1992 | Brown et al. | 424/450 |
| 5,152,990 | 10/1992 | Miyauchi | 424/400 |
| 5,183,817 | 2/1993 | Bazzano | 514/256 |
| 5,276,056 | 1/1994 | Leroy | 514/567 |
| 5,597,575 | 1/1997 | Breitbarth | 424/401 |
| 5,641,480 | 6/1997 | Vermeer | 424/70.24 |
| 5,660,818 | 8/1997 | Dubief et al. | 424/70.1 |
| 5,674,510 | 10/1997 | Ditucci | 424/401 |
| 5,741,481 | 4/1998 | Picken, Jr. | 424/74 |

FOREIGN PATENT DOCUMENTS

| | | |
|---|---|---|
| 05221844 | 8/1993 | Japan . |
| 203556 | 4/1993 | Taiwan . |

*Primary Examiner*—Jean C. Witz
*Attorney, Agent, or Firm*—Brian S. Steinberger; Law Offices of Brian S. Steinberger

[57] ABSTRACT

A topical hair growing solution having selected portions of rice and wheat bran, zymotic vegetable flour enzyme, water and and a citrus extract such as P-50 (grapefruit seed extract). The components are mixed thoroughly, allowed to ferment, mixed again together and micro filtrated, after which the grapefruit seed extract is then added. The novel mixture is applied to the scalp and encourages hair follicles to grow. Other benefits include eliminating dandruff, psoriasis, and scalp itching, burning and dryness when applied after hair coloring.

13 Claims, No Drawings

HAIR AND SCALP NOURISHING COMPOSITION

This invention relates to topical hair applications, and in particular to a hair growing mixture solution that is applied to the scalp.

BACKGROUND AND PRIOR ART

Baldness and thinning hair can come with age, by genetic predisposition, clogged pores, viruses, and the like. More specifically, excess male hormones, dirty scalps(from dandruff, itching, etc.), low metabolism, tension of the scalp, stress and heredity are known factors for thinning hair and baldness. Over the years various preparations have been proposed for the treatment of baldness usually with poor results. The most infamous and successful as been minoxidil. See column 1 of U.S. Pat. No. 5,183,817 to Bazzano, which is incorporated by reference. However, minoxidol is a very expensive medication that only provides success rates of no more than up to approximately 1/3 of users of the application.

Other preparations involving artificial concoctions, vitamins, minerals, and like solutions have been applied with no more success. See for example U.S. Pat. No. 5,741,481 to Picken, Jr.; U.S. Pat. No. 5,674,510 to DiTucci; U.S. Pat. No. 5,660,818 to Dubief; U.S. Pat. No. 5,641,480 to Vermeer; U.S. Pat. No. 5,597,575 to Breitbarth; U.S. Pat. No. 5,276,056 to Le Roy; U.S. Pat. No. 5,183,817 to Bazzano; and U.S. Pat. No. 5,152,990 to Miyauchi.

SUMMARY OF THE INVENTION

The first objective of the present invention is to provide an all natural topical application for the scalp for promoting new hair growth for male and female users.

The second object of this invention is to provide an all natural topical application for the scalp that nourishes and thickens thinning hair.

The third object of this invention is to provide an all natural topical application for the scalp that helps prevent dandruff.

The fourth object of this invention is to provide an all natural topical application for the scalp that helps prevent scalp itching.

The fifth object of this invention is to provide an all natural topical application for the scalp that promotes healthier hair that is stronger, shinier and more manageable.

The sixth object of this invention is to provide an all natural topical application for the scalp that eliminates yellowish stained color from gray hair.

The seventh object of this invention is to provide a topical solution for the scalp after coloring hair for soothing and reducing irritation to the scalp and feelings of tightening of the scalp.

The eighth object of this invention is to provide a topical solution for the scalp that eliminates psoriasis on the scalp.

A preferred mixture of the hair growing mixture includes mixing bran, vegetable enzyme; water, and a citrus fruit extract, wherein the mixture when applied to the scalp encourages hair follicles to grow. The bran can be rice bran and wheat bran. The vegetable enzyme can be zymotic vegetable flour enzyme. The water can be distilled water, spring water and tap water, and the citrus fruit extract can be P-50 grapefruit seed extract. Alternative citrus fruit extract can be sodium sulfites and ascorbic acid. A exemplary mixture includes approximately 5 lbs of bran, approximately 500 grams of the vegetable enzyme, approximately 2.75 gallons of water, and approximately 4 teaspoons of approximately 0.5% strength of citrus extract.

A preferred method of preparing the hair growing solution includes: (a) mixing together bran and an vegetable enzyme to form a first mixture, (b) mixing the first mixture with water to form a second mixture, (c) fermentating the second mixture for a first selected time at a first selected temperature, (d) remixing the fermentated second mixture into a third mixture, if necessary, (e) fermentating the third mixture for a second selected time and a second selected temperature, (f) refrigerating the fermentated third mixture into a refrigerated mixture, (g) collecting non-sediment solution the refrigerated mixture, (h) filtering the non-sediment solution, (i) mixing a citrus seed extract with the filtered non-sediment solution to form a hair growing mixture, and (j) applying the hair growing mixture to the scalp to encourage hair to grow.

The novel mixture can be applied after coloring the hair, wherein the mixture soothes scalp irritations caused by the coloring of the hair.

Each hair lies in a follicle. Each follicle operates on its own time table, where each follicle acts on its own. For example, each follicle has its own life where the individual follicle grows, rests, and falls out. Since each follicle has its own life, all hair does not grow simultaneously. Therefore, it takes time grow back hair throughout one's scalp. At the base of the follicle is the papilla, which provides nourishment for new cells forming at the base of the root. Within a hair's life cycle, it will grow, rest, and fall out, either on its own or by being pushed out by a new strand of hair. The novel all natural hair growing mixture provides nutrients directly to the papilla, resulting in the growth of new hair.

Further objects and advantages of this invention will be apparent from the following detailed description of a presently preferred embodiment.

DESCRIPTION OF THE PREFERRED EMBODIMENT

Before explaining the disclosed embodiment of the present invention in detail it is to be understood that the invention is not limited in its application to the details of the particular arrangement shown since the invention is capable of other embodiments. Also, the terminology used herein is for the purpose of description and not of limitation.

To obtain approximately one gallon of the topical solution, a preferred list of the ingredients listed in Table I are used.

TABLE 1

| Substance | Amount |
| --- | --- |
| Rice Bran | 5 lbs |
| Zymotic vegetable flour enzyme | 500 grams |
| Distilled Water | 2.75 gallons or 2 gallons 96 oz(maximum volume) |
| P-50 grapefruit seeds extract | 0.5% strength of 4 teaspoons to be added into the final collected solutions |

Alternative to rice bran listed above, a like amount of wheat bran can be used. Alternative to distilled water, tap water, spring water can be used. Alternative to P-50 grapefruit seeds extract, sodium sulfites and ascorbic acid can be used.

A preferred embodiment of the invention mixture includes step (1) mixing rice bran and vegetable flour together to form a first mixture(The rice bran and the vegetable flour can be initially mixed manually in a glass jar or a plastic jar using a stainless steel spoon. Alternatively, the rice bran and the vegetable flour can be initially mixed in a plastic bag by shaking the contents and then pouring the mixture into a glass or plastic jar); (2) add distilled water to the first mixture, making sure the bran and vegetable flour are completely dissolved in the water to form a second mixture; (3) Allow the second mixture to fermentate in closed containers at temperatures of approximately 72 to approximately 76 degrees F.; (4) remix the second mixture thoroughly; (5) fermentate the second mixture a second time for approximately 2 to approximately 4 hours at approximately 72 to approximately 76 degrees F.; (6) remix the second fermentation a second time, if necessary; (7) fermentate for a third time, if necessary, the resulting mixture for approximately 2 to approximately 4 hours at approximately 72 to approximately 76 degrees F.; (8) refrigerate the third fermentation at temperatures of approximately 40 F. to approximately 45 F.; (9) keep jar in refrigerator until sediment appears to settle at the bottom(up to approximately ½ a day); (10) After sediment goes to the bottom, collect liquid at top(for example by pouring the contents through a fine meshed strainer); (11) Pass liquid through micro-filtrations (i.e. commercially available paper filter); and (12) Add P-50 Grapefruit Seed extract natural preservative (P-50 is a non-metallic organic anti microbial and anti fungal compound that is in a heavy liquid viscous form having a lemon yellow color).

The method steps of applying the novel topical application will now be described. On a daily basis for approximately four months.

STEPS (1) Massage the entire head for approximately 30 to approximately 40 seconds before applying. Massaging can be done by pressing the head lightly by both hands and fingers starting from the back and moving to the front of the head.
(2) With a cotton ball saturated with the invention mixture, pat lightly the entire scalp even where there is hair.
(3) Massage entire scalp for approximately 30 to approximately 40 seconds, with the same procedure as done in step(1).
(4) Wait approximately 20 minutes, then shampoo with a mild shampoo. Rinse hair out thoroughly. Pat dry hair with towel.

After approximately four months, hair growth should occur and other benefits listed in the summary portion of this invention will occur. Results improve as users continue using hair growth solution. It takes time to regrow hair. Users are to continue these steps to maintain hair and hair growth as long as it takes. Each follicle operates on its own timetable. Once users reach a desired level of hair, they just keep up to maintain hair by using the novel mixture every other day or at least twice per week. The summary of the this invention shows that the novel mixture is not just for thinning hair or baldness.

A test subject had large bald shiny spots on his head for years. Using the above steps, a gradual change occurred in the texture of the scalp by approximately the second to third month of application. The smooth shiny slick scalp of the user started to lose that particular shininess and the scalp started to develop hair pores and sprout hair follicles. The user had started the process with a ring of gray hair around his head that was tainted with a yellowish stain. After approximately the second to third month of application, the user's hair lost that dirty yellowish stain and became clean white hair. Furthermore, the user started the process with spots of psoriasis on their head. After using the novel mixture, the psoriasis disappeared. This test subject has been applying the novel mixture since approximately Jan. 15, 1997 and as of Jul. 4, 1998 has restored substantially much of his lost hair. It is anticipated that most of the subject testers hair will be fully restored within approximately two to approximately 2 & ½ years.

The inventor of this subject invention has used the subject invention as well. The inventor colors and perms their hair with a coloring solution that has made their scalp dry, burning and irritating. The subject inventor used to take a topical application entitled: Seldane™ to stop the dry, burning and irritating effects. Furthermore, the inventor also suffered from dandruff. The inventor started applying the novel mixture invention right after coloring their hair using the above application steps, and then waited approximately 20 minutes before shampooing. After a single application, all the dryness, burning and irritation effects stopped and no more dandruff was visible.

In addition to using the novel invention preparation several other procedures can be done. First, the scalp should be massaged daily for a few times a day for blood circulation. Next, the scalp and hair need to be kept clean by being washed daily. Furthermore, the user should get enough rest(approximately 8 hours per night) and avoid stress. Furthermore, the user needs to maintain nutritional balance rich in protein, vitamins, and minerals. The subject inventor has found that the added nutritional diet should include vitamins such as but not limited to Biotin, Pantothenic acid, and minerals such as but not limited to Zinc.

The novel invention mixture can be applied any time of the day. Over time, users can achieve the benefits described previously described above. Users can enjoy healthier, shinier, stronger and manageable hair since the novel invention mixture nourishes the scalp and hair, and reduces scalp itching, and the like.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A hair and scalp nourishing composition comprising the combination of effective amounts of
    bran;
    vegetable enzyme,
    water; and
    P-50 grapefruit seed extract, wherein the composition when applied to the scalp stimulates growth of existing hair follicles.
2. The composition of claim 1, wherein the bran is selected from the group consisting of rice bran and wheat bran.
3. The composition of claim 1, wherein the vegetable enzyme comprises zymotic vegetable flour enzyme.
4. The composition of claim 1, wherein the water is selected from the group consisting of distilled water, spring water and tap water.
5. The composition of claim 1, wherein the P-50 grapefruit seed extract comprises sodium sulfites.
6. The composition of claim 1, wherein the P-50 grapefruit seed extract comprises ascorbic acid.

7. The composition of claim 1 wherein the amount of bran is approximately 5 lbs., the amount of vegetable enzyme is approximately 500 grams, the amount of water is approximately 2.75 gallons, and the amount of P-50 grapefruit seed extract is approximately 4 teaspoons of approximately 0.5% strength.

8. A method of preparing a hair and scalp nourishing composition for topical application to a scalp, comprising the steps of:

(a) mixing together bran and a vegetable enzyme to form a first mixture;

(b) mixing the first mixture with water to form a second mixture;

(c) storing the second mixture for a selected time and a selected temperature;

(d) remixing the second mixture to form a third mixture;

(e) storing the third mixture for a selected time and a selected temperature;

(f) refrigerating the third mixture to form a refrigerated mixture;

(g) collecting a non-sediment solution from the refrigerated mixture;

(h) filtering the non-sediment solution; and (i) mixing P-50 grapefruit seed extract with the filtered non-sediment solution to form the composition.

9. The method of claim 8, wherein the bran of step (a) is selected from the group consisting of rice bran and wheat bran.

10. The method of claim 8, wherein the vegetable enzyme of step (a) comprises zymotic vegetable flour enzyme.

11. The method of claim 8, wherein the water of step (b) is selected from the group consisting of distilled water, spring water, and tap water.

12. The method of claim 8, wherein the P-50 grapefruit seed extract comprises sodium sulfites and/or ascorbic acid.

13. The method of claim 8, wherein the amount of bran is approximately 5 lbs., the amount of vegetable enzyme is approximately 500 grams, the amount of water is approximately 2.75 gallons, and the amount of P-50 grapefruit seed extract is approximately 4 teaspoons of approximately 0.5% strength.

* * * * *